US011187656B2

(12) United States Patent
Heller et al.

(10) Patent No.: US 11,187,656 B2
(45) Date of Patent: Nov. 30, 2021

(54) METHODS AND DEVICES FOR DETERMINING A GUEST STRUCTURE ON A HOST STRUCTURE

(71) Applicant: LUMICKS DSM HOLDING B.V., Amsterdam (NL)

(72) Inventors: Iddo Heller, Amsterdam (NL); Anna Elisabeth Christina Meijering, Amsterdam (NL); Gijs Jan Lodewijk Wuite, Amsterdam (NL); Erwin Johannes Gerard Peterman, Amsterdam (NL); Andreas Sebastian Biebricher, Amsterdam (NL)

(73) Assignee: LUMICKS DSM HOLDING B.V.

( * ) Notice: Subject to any disclaimer, the term of this patent is extended or adjusted under 35 U.S.C. 154(b) by 0 days.

(21) Appl. No.: 16/967,111

(22) PCT Filed: Feb. 5, 2019

(86) PCT No.: PCT/NL2019/050071
§ 371 (c)(1),
(2) Date: Aug. 3, 2020

(87) PCT Pub. No.: WO2019/151864
PCT Pub. Date: Aug. 8, 2019

(65) Prior Publication Data
US 2021/0080394 A1    Mar. 18, 2021

(30) Foreign Application Priority Data
Feb. 5, 2018 (NL) ..................................... 2020377

(51) Int. Cl.
*C12Q 1/68* (2018.01)
*G01N 15/06* (2006.01)
(Continued)

(52) U.S. Cl.
CPC ..... *G01N 21/6428* (2013.01); *G01N 21/6402* (2013.01); *G01N 21/6458* (2013.01);
(Continued)

(58) Field of Classification Search
CPC .... G16B 15/00; G01N 21/6428; G01N 21/76; G01N 21/75; G01N 21/6458;
(Continued)

(56) References Cited

U.S. PATENT DOCUMENTS 5,936,731 A * 8/1999 Cabib ...................... A61B 3/12
356/456
6,043,039 A * 3/2000 Bar-Am ................ C12Q 1/6841
435/6.11

FOREIGN PATENT DOCUMENTS

| WO | WO9310266 A1 | 5/1993 |
| WO | WO9722848 A1 | 6/1997 |
| WO | WO2014200341 A1 | 12/2014 |

OTHER PUBLICATIONS

International Search Report and Written Opinion for corresponding International application No. PCT/NL2019/050071 dated May 31, 2019 (15 pages).
(Continued)

*Primary Examiner* — Brian J. Sines
(74) *Attorney, Agent, or Firm* — Mendelsohn Dunleavy, P.C.

(57) ABSTRACT

One aspect of this disclosure relates to a method for determining a presence of at least one guest structure at a host structure. The method comprises a light-sensitive system receiving light from the host structure. The host structure hosts one or more optically active entities at at least one part of the host structure. Herein, the at least one part does not host the at least one guest structure. Furthermore, the optically active entities cause light emission from said at least one part. The method also comprises the light-sensitive
(Continued)

system outputting a signal based on the received light. The method further comprises determining a light value based on the output signal. The light value indicates an amount of light from the host structure being incident on the light-sensitive system. The method also comprises determining on the basis of the light value at least one of a quantity and a position of the at least one guest structure at the host structure.

20 Claims, 6 Drawing Sheets

(51) Int. Cl.
| | |
|---|---|
| *G01N 33/00* | (2006.01) |
| *G01N 21/00* | (2006.01) |
| *G01N 21/64* | (2006.01) |
| *G01N 21/66* | (2006.01) |
| *G01N 35/00* | (2006.01) |
| *G16B 15/00* | (2019.01) |
| *G06K 9/00* | (2006.01) |
| *G06K 9/32* | (2006.01) |

(52) U.S. Cl.
CPC ....... *G06K 9/00134* (2013.01); *G06K 9/3233* (2013.01); *G16B 15/00* (2019.02); *G01N 2201/0633* (2013.01); *G01N 2201/06113* (2013.01)

(58) Field of Classification Search
CPC .... G01N 15/06; G01N 21/6402; G01N 33/00; G01N 35/00; G01N 2201/06113; G01N 33/48; G01N 21/66; G01N 2201/0633; G01N 21/00; G01N 21/64; G06K 9/00134; G06K 9/3233; C12Q 1/68
See application file for complete search history.

(56) References Cited

OTHER PUBLICATIONS

Ashkin, Arthur, et al. "Observation of a single-beam gradient force optical trap for dielectric particles" Optics Letters 11.5 (1986): 288-290.

Boger, Dale L., et al. "A Simple, High-Resolution Method for Establishing DNA Binding Affinity and Sequence Selectivity." Journal of the American Chemical Society 123.25 (2001): 5878-5891.

Brouwer, Ineke, et al. "Human RAD52 Captures and Holds DNA Strands, Increases DNA Flexibility, and Prevents Melting of Duplex DNA: Implications for DNA Recombination." Cell Reports 18.12 (2017): 2845-2853.

Brouwer, Ineke, et al. "Sliding sleeves of XRCC4-XLF bridge DNA and connect fragments of broken DNA." Nature 535.7613 (2016): 566-569.

Candelli, Andrea, et al. "Combining optical trapping, fluorescence microscopy and micro-fluidics for single molecule studies of DNA-protein interactions." Physical Chemistry Chemical Physics 13.16 (2011): 7263-7272.

Mortensen, Kim I, et al. "Optimized localization analysis for single-molecule tracking and super-resolution microscopy." Nature Methods 7.5 (2010): 377-381.

Zaitsev, Eugene N., et al. "Binding of double-stranded DNA by *Escherichia coli* RecA protein monitored by a fluorescent dye displacement assay." Nucleic Acids Research 26.2 (1998): 650-654.

\* cited by examiner

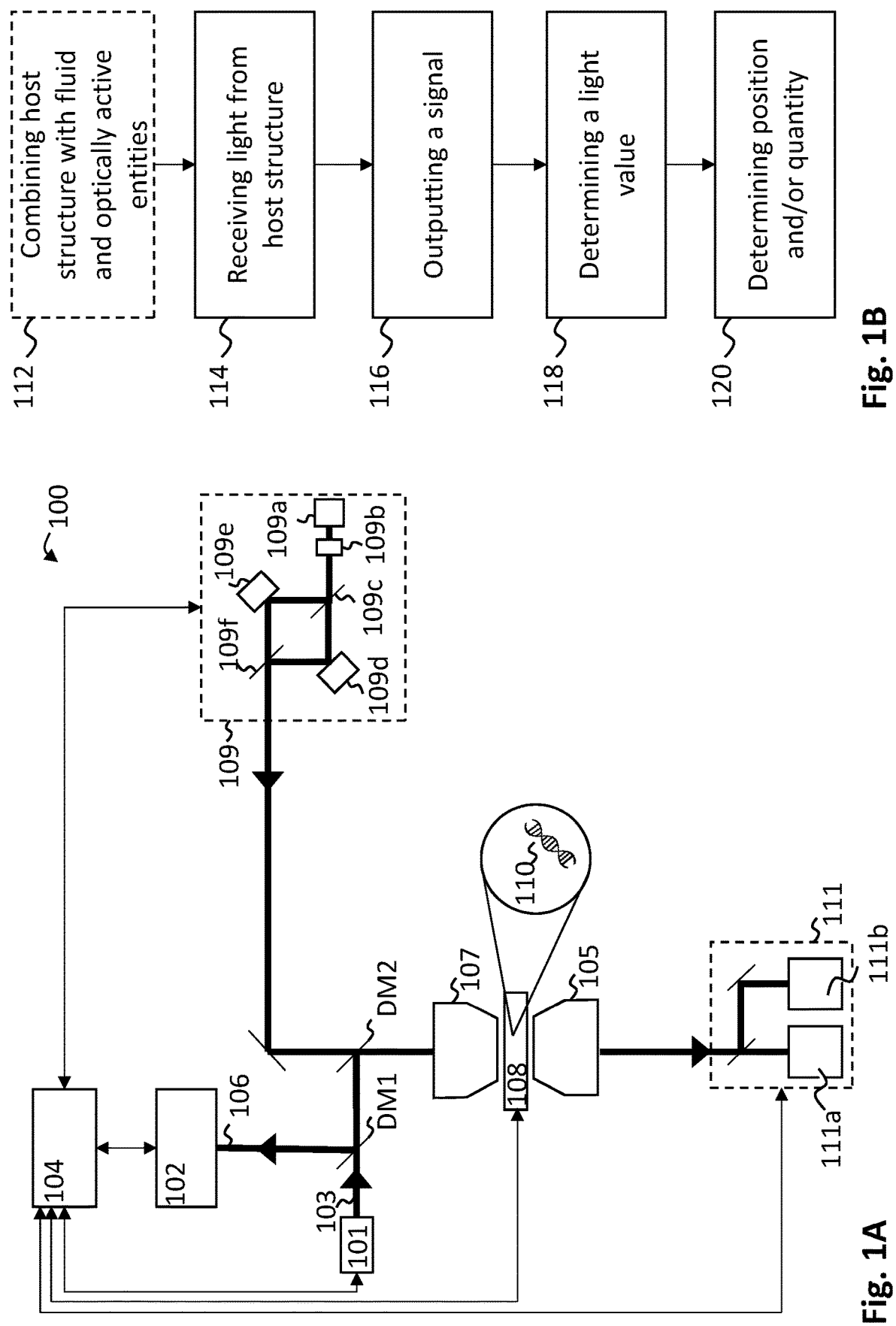

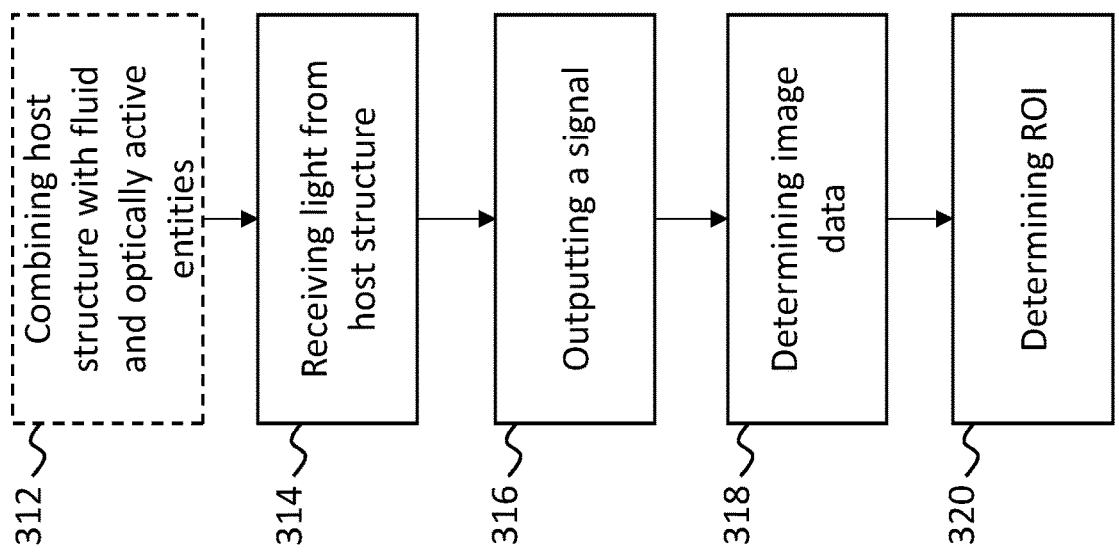
Fig. 3
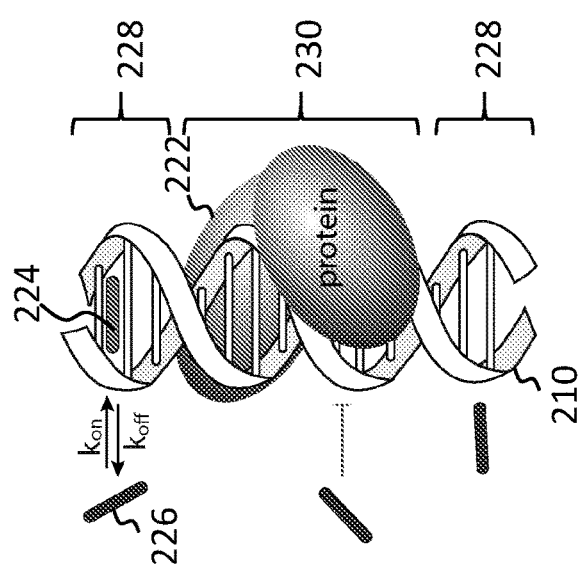
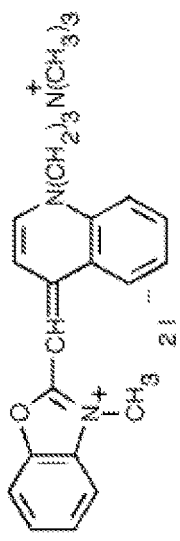
YO-PRO1
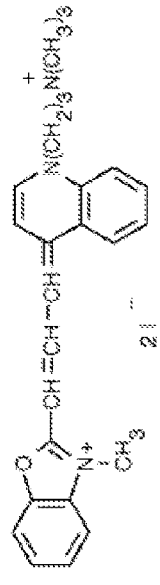
YO-PRO3
Fig. 2

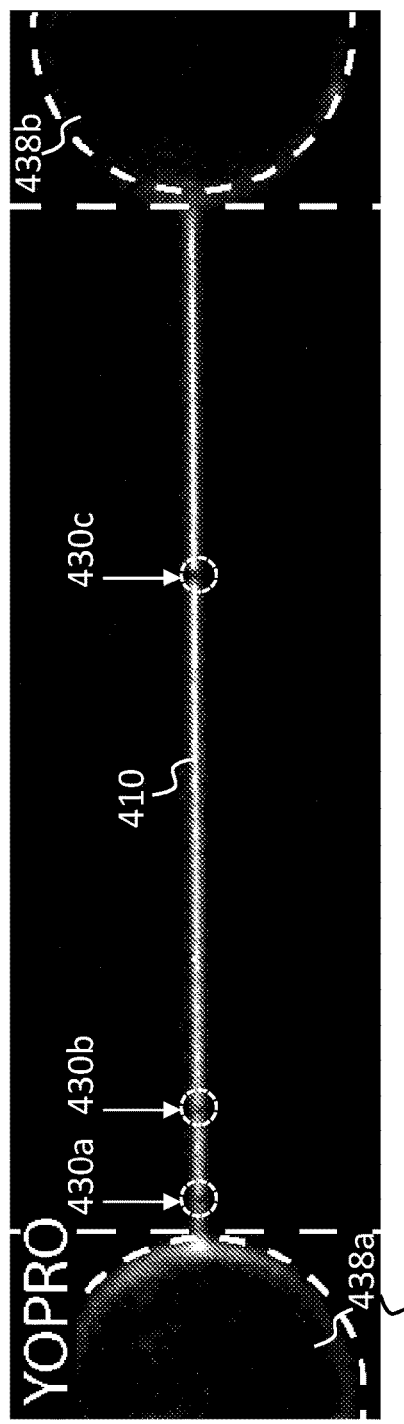
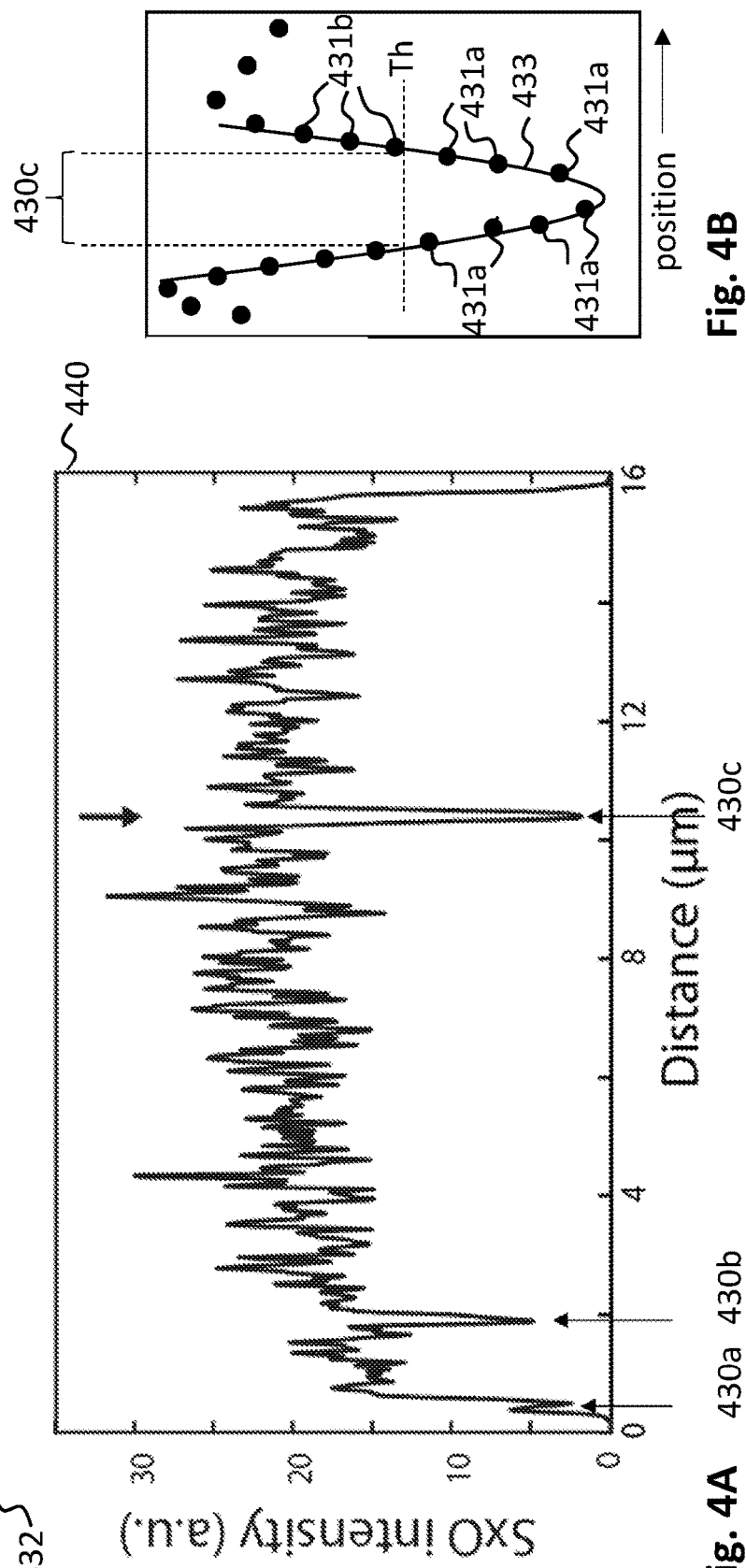
Fig. 4A
Fig. 4B

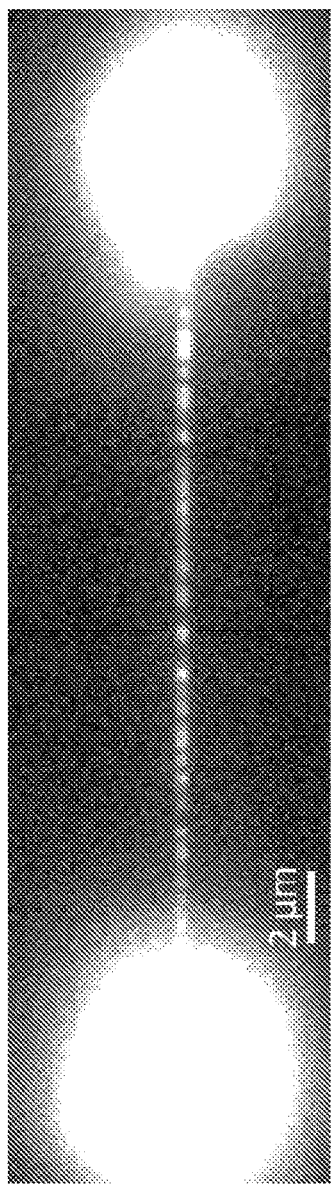
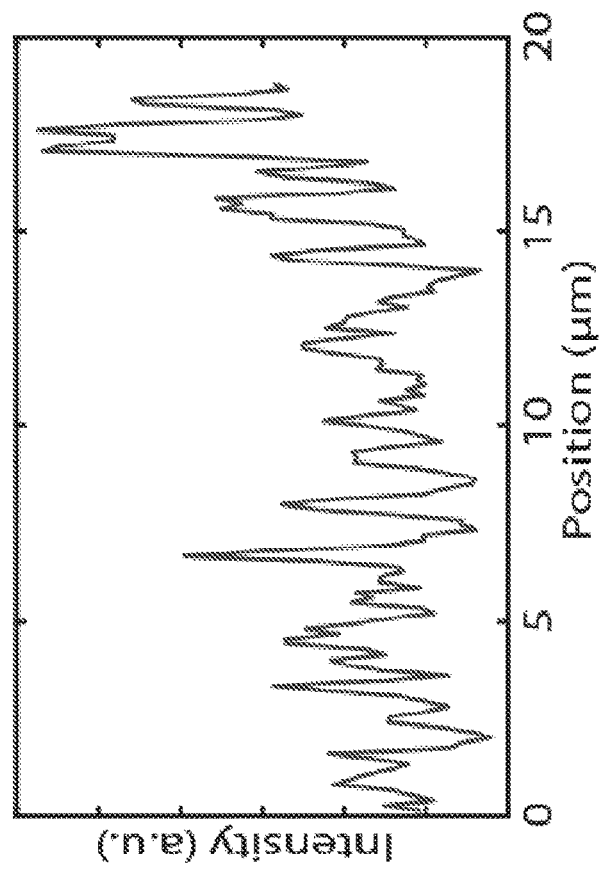
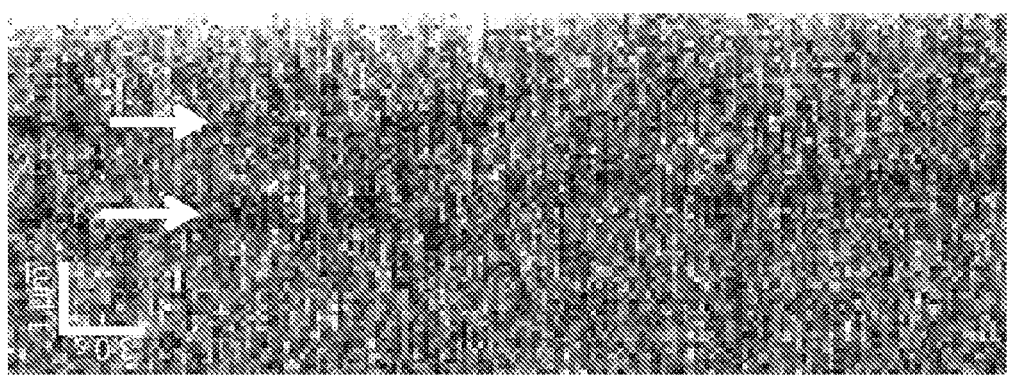
Fig. 7

METHODS AND DEVICES FOR DETERMINING A GUEST STRUCTURE ON A HOST STRUCTURE

FIELD OF THE INVENTION

This invention relates to methods, systems and computer programs for determining a presence of a guest structure, such as a protein or complex of proteins, at a host structure, such as a DNA molecule.

BACKGROUND

Analysis of host structure-guest structure interactions is of ever increasing importance, for example for unravelling the details of a wide range of DNA-associated processes. Candelli, Wuite, & Peterman, Phys. Chem. Chem. Phys., 2011, 13, 7263-7272) provides a method for such analysis. Herein, fluorescently labelled EcoRV enzymes are visualized that are stably bound to a dsDNA molecule. To this end, epi-illuminated wide-field fluorescence microscopy is used. Furthermore, the dsDNA molecule is held between two optically trapped microspheres in a stretched configuration, at a tension of 40 pN. This method enables to determine the binding positions of the EcoRV restriction enzyme, a guest structure, on the dsDNA molecule, the host structure.

However, disadvantageously this method requires the use of labelled guest structures, in this case labelled enzymes. The guest structures thus have to be labelled before they can be studied. Unfortunately, labelling a guest structure can be challenging and cumbersome, for example because it may include labour-intensive sample preparation or genetic modification of the guest structure.

Also, the above described method in principle can only be applied to study labelled guest structures. However, labelling is not by definition possible for any given guest structure. Hence, the above-described method can only be applied to study a limited number of guest structures.

Furthermore, labelling a guest structure may impede an accurate analysis. Labelling a guest structure may influence the guest structure's properties under scrutiny. In an example, labelling a protein or complex of proteins with a fluorescent entity may change its binding properties in respect of a DNA-molecule, which impedes accurate analysis of these binding properties. Labelling can also alter the guest structure's shape or its activity. Furthermore, the labelling is not complete in the sense that not all guest structures involved in an experiment are labelled, as a result of which guest-structures may remain unnoticed when residing at the host structure.

Thus, there is a need in the art for improved methods for analysing host structure-guest structure interactions that alleviate at least some of the above-identified problems.

SUMMARY

To that end, one aspect of this disclosure relates to an, optionally computer-implemented, method for determining a presence of at least one guest structure at a host structure. The method comprises a light-sensitive system receiving light from the host structure. The host structure hosts one or more optically active entities at at least one part of the host structure. Herein, the at least one part does not host the at least one guest structure. Furthermore, the optically active entities cause light emission from said at least one part. The method also comprises the light-sensitive system outputting a signal based on the received light. The method further comprises determining a light value based on the output signal. The light value indicates an amount of light from the host structure being incident on the light-sensitive system. The method also comprises determining on the basis of the light value at least one of a quantity and a position of the at least one guest structure at the host structure.

The guest structure and/or the host structure may be a biological structure, in particular a microbiological structure and/or a cellular and/or subcellular structure. The guest structure for example is a protein or complex of multiple proteins and the host structure a DNA molecule. The optically active entities may comprise DNA intercalator molecules. Alternatively, the host structure may be a cell membrane comprising lipid molecules and the one or more optically active entities may comprise a fluorescently labeled lipid molecule that can move in/through the cell membrane.

The host structure locally not hosting optically active entities may be a consequence of the host structure locally hosting guest structures. The host structure hosting the guest structure may be understood to comprise the host structure being bound to the guest structure, for example with one or more chemical bonds, such as covalent bonds, and/or hydrogen bonds and/or other strong interactions, such as ionic bonds, polar bonds and/or weak interactions such as Vander-Waals forces, electrostatic forces, forces due to hydrophobicity/hydrophilicity. Such a bond may locally change the binding properties of the host structure as a result of which the host structure can host a reduced number of optically active entities. In an example, such a bond may prevent the host structure from hosting any optically active entity at the position of the bond.

The optically active entities may cause light emission from the at least one part that is not hosting the at least one guest structure, as a result of the optically active entities being positioned at the at least one part in addition to the optically active entities emitting light. The optically active entities may emit light in response to absorbing excitation light. In an example, the optically active entities are fluorescent entities that emit fluorescent light. Since, the presence of a guest structure at a particular position may at least reduce the number of optically active entities at the particular position, the host structure may at this particular position emit less light towards the light-sensitive system.

Optically active may be understood to relate to any process comprising a light-matter interaction including but not limited to absorption, fluorescence, changing of polarization, phosphorescence, bioluminescence, phase retardation, stimulated emission, etc.

The light value may indicate an amount of light in the sense that it indicates a number of photons incident on the light-sensitive system and/or a light intensity incident on at least part of the light-sensitive system.

The method enables to more accurately study interactions between a guest structure and a host structure. Advantageously, the disclosed method does not require any labelling of the guest structure. Hence, the drawbacks associated with labelling guest structures are alleviated. The number of biochemical labeling steps are reduced and such steps may even be avoided completely. Further, the disclosed method enables to study a wide variety of guest structures, for example wildtype proteins instead of labeled proteins, which not only increases the accuracy of the analyses because their properties are not influenced by a label but also enhances the biological relevance of such studies. Furthermore, the method does not require to permanently label the host or guest structure, which prevents problems associated with photobleaching and/or photodamage of permanent labels involved.

The method does not require labelling of the guest structure, because the host structure hosts optically active entities at parts that are not hosting a guest structure. The guest structures and the optically active entities may be understood to be in competition for positions at the host structure in the sense that the host structure cannot, at least to a lesser extent, simultaneously host a guest structure and an optically active entity at the same position. This may be a consequence of the guest structure occupying binding sites at the host structures and/or of steric interactions between the guest structure and at least one of the optically active entities at the host structure. Thus, the light emission from the host structure, which light is caused by the optically active entities, may thus distinguish between parts of the host structure hosting a guest structure and parts not hosting a guest structure. In this method, the parts not hosting a guest structure are labelled instead of the guest structures themselves, however, the presence of the guest structures can still be determined. Furthermore, since the guest structures are not labeled, unbound guest structures do not cause background light. Hence, high concentrations of guest structures may be used in experiments without a significant decrease of signal-to-noise ratios. Also, labeled guest structures can adopt dark and bleached states, which negatively impacts the ability to observe these labeled guest structures, for example because it impedes using long imaging times. The method thus also allows for imaging the guest structures during longer periods of time without being hindered by the guest structures bleaching or adopting a dark state. These longer periods allow to better study dynamics, such as mobility and/or binding rates of the guest structures.

In one embodiment, the method comprises determining a binding property of the at least one guest structure in respect of the host structure on the basis of the light value.

The light-sensitive system may continuously output the signal, which allows determining a plurality of light values, wherein the plurality of light values indicate the amount of light from the host structure incident on the light-sensitive system at respective times. Then, based on these light-values, respective quantities of the at least one guest structure at different times may be determined.

A binding property may comprise determining the rate at which the quantity of the at least one guest structure hosted by the host structure changes in time.

This embodiment enables to measure further physical properties of the guest structure in relation to the host structure.

In one embodiment, the light-sensitive system is part of a microscope, e.g. a fluorescence microscope. In this embodiment, the method comprises determining the light value based on the output signal in the sense that the method comprises determining image data based on the output signal, the image data representing an image of at least part of the host structure and comprising a plurality of image pixel values associated with respective parts of the host structure. Each image pixel value indicates an amount of light from its associated part of the host structure incident on the light-sensitive system. Further, in this embodiment, the method comprises determining on the basis of the light value the position of the guest structure at the host structure in the sense that the method comprises determining at least one region of interest (ROI) comprising at least one image pixel value in the image on the basis of the image pixel values.

The at least one ROI in the image indicates the position of the at least one guest structure at the host structure.

The ROI may thus represent a part of the host structure, which part is hosting a guest structure. Typically, if for example fluorescent optically active entities are used, the ROI in the image appears as a relatively "dark" region or shadow in the image and typically the ROI comprises a plurality of image pixel values.

Preferably, the optically active entities can be hosted at the host structure at closely spaced binding sites simultaneously at one time or distributed over a plurality of times such that the sampling density on the host structure is high. Higher sampling density enables more accurate and/or more probable localization of guest structures and/or allows detection of smaller guest structures.

This embodiment enables to accurately determine the position of at least one guest structure at the host structure using image processing techniques. The accuracy depends amongst others on the resolution of the employed microscope.

In one embodiment, determining the at least one ROI in the image comprises determining that said at least one image pixel value of the ROI is indicative of an amount of light that is lower than a threshold amount of light.

In this embodiment, the method may comprise comparing the at least one image pixel value with a threshold pixel value indicating said threshold amount of light. Herein, the threshold pixel value may be predetermined.

In case the ROI comprises a plurality of image pixel values, each of these image pixel values may indicate an amount of light that is lower than a threshold amount of light.

This embodiment enables efficient processing of the image data for determining the position of the guest structure.

In one embodiment, the method comprises determining a threshold pixel value indicating the threshold amount of light on the basis of the image data. In this embodiment, determining that said at least one image pixel value is indicative of the amount of light lower than the threshold amount of light comprises comparing the at least one image pixel value with the threshold pixel value.

This embodiment may comprise determining that the at least one image pixel value of the ROI is lower or higher than the threshold pixel value and in response determining the ROI.

This embodiment enables to determine the ROI in the image data substantially based on the image data. Aberrant image pixel values, for example relatively low image pixel values, in the image data may be identified for determining the ROI.

In one embodiment, determining the threshold pixel value comprises determining an average and a variation of image pixel values that are associated with respective parts of the host structure not hosting a guest structure. This embodiment further comprises, based on the determined average and variation, determining the threshold pixel value. This embodiment allows to easily determine the threshold pixel value.

In one embodiment, determining the image data based on the output signal comprises determining for a plurality of time periods respective subsets of image data based on the output signal. Each subset of image data represents an image of at least part of the host structure during respective time periods and each subset of image data comprises a plurality of image pixel values associated with respective parts of the host structure. Furthermore, each image pixel value in a subset of image data indicates an amount of light from its associated part of the host structure that is incident on the light-sensitive system during its associated time period. This embodiment further comprises determining the image data based on the subsets of image data.

In one embodiment, each subset of image pixel values comprises a plurality of image pixel values associated with a light-emitting event during the time period. In this embodiment, determining the image data based on the subsets of image data comprises, for each light-emitting event in the subsets of image data, fitting a point spread function, e.g. the point spread function associated with the light-sensitive system, to its plurality of image pixel values for determining a position of each light-emitting event. The fitting optionally comprises selecting an amplitude and/or width of the point spread function.

In a further embodiment, the method comprises, for each light-emitting event in the subsets of image data, determining on the basis of the fitted point spread function, in particular on its amplitude and or width, an event localization curve indicating a position of the light-emitting event. In this embodiment, determining the image data comprises summing the determined event localization curves.

Determining an event localization curve may comprise determining a width of the event localization curve on the basis of the selected amplitude. Herein, the width may be related to the accuracy with which the position of the light-emitting event can be determined. It should be appreciated that a larger amplitude of the fitted point spread functions indicates that more photons were captured associated with the light-emitting event. Larger amplitudes may thus be associated with higher signal-to-noise ratios. Hence, larger amplitudes may justify determining a smaller width of the event localization curve and thus to more accurately determine the position of a light-emitting event and thus of a guest structure. This embodiment allows to use super-resolution localization microscopy.

In one embodiment, the method comprises determining a first and second ROI in the image on the basis of the image pixel values, the first and second ROI each comprising at least one image pixel value and the first ROI in the image indicating a position of a first guest structure at a host structure and the second ROI in the image indicating a position of the second guest structure at a host structure. The first and second guest structures need not necessarily be hosted on the same guest structure. In principle, a plurality of host structures may be imaged simultaneously, each of the host structures hosting at least one guest structure. This embodiment thus enables to determine the positions of multiple guest structures at one or more host structures.

In one embodiment, a fractional occupation, e.g. a fractional coverage, of the host structure by the optically active entities is kept below 20%, preferably below 15%, more preferably below 10%, most preferably below 5%. The fractional coverage may be kept below a certain level with the aim to limit perturbation of a host structure-guest structure interaction by the presence of the optically active entities at the host structure.

The fractional occupation of the host structure by the optically active entities may be below a certain percentage preferably at least while the light-sensitive system is receiving the light from the host structure.

The fractional coverage may be defined as a ratio between an amount of optically active entities 224 being hosted by host structure 210 and an amount of optically active entities 224 that the host structure 210 can (approximately) maximally host.

The fractional occupation of the host structure by the optically active entities may be below a particular percentage preferably at least while the light-sensitive system is receiving the light from the host structure, e.g. during an experiment.

This embodiment enables to more accurately determine the binding properties of the guest structure in respect of the host structure. By limiting the fractional occupation of the host structure by the optically active entities, it can be ensured that there is sufficient room at the host structure for guest structures of interest to position themselves, without being influenced too much by the presence of the optically active entities. In an example, the fractional occupation relates to a fractional coverage, which is kept below a specific percentage such that sufficient binding sites are available to which guest structures of interest can bind. Therefore, the binding properties of the guest structure of interest are to a lesser extent influenced by optically active entities that are already bound to the host structure.

In one embodiment, the method comprises performing a baseline measurement. To this end, the method comprises the light-sensitive system receiving reference light from the host structure hosting one or more optically active entities, wherein the optically active entities cause light emission from the host structure and wherein the host structure hosts a reference quantity of guest structures. In one example, the host structure does not host any guest structure. In this embodiment, the method comprises the light-sensitive system outputting a reference signal based on the received reference light and determining a reference light value based on the output signal. The reference light value indicates an amount of light from the host structure being incident on the light-sensitive system. In this embodiment, the method further comprises determining on the basis of the light value and of the reference light value at least one of the quantity and the position of the at least one guest structure at the host structure.

The baseline measurement may reduce the number of false positives. A host structure may namely comprise parts that inherently exhibit low light emission, irrespective of whether such parts host a guest structure or not. Such parts may be identified during the baseline measurement, which prevents falsely identifying a guest structure at such parts of the host structure.

This embodiment enables more accurate analyses of the guest structures, because the quantity and/or position of the at least one guest structure is performed based on both the light value and the reference light value.

In one embodiment, the host structure is at least partially positioned in a fluid comprising optically active entities. The optically active entities being configured to transiently bind to the host structure.

The optically active entities may exhibit an off-rate binding constant in respect of the host structure that is preferably equal to or larger than a rate at which events of a process under scrutiny occur.

As a result of the transient binding of the entities, the entities do not permanently occupy a binding site, as a result of which binding rates of the guest structures in respect of the host structure can be more accurately determined as well as a movement of the guest structure on the host structure.

In one embodiment, the method comprises controlling a force application system to apply a tension to the host structure for at least one of
controlling the signal that is output by the light-sensitive system
suppressing a motion of the host structure, and
positioning, e.g. orienting, the host structure.

This embodiment enables to tune the signal that is output by the light-sensitive system. The binding properties of the optically active entities and hence the light emission by these entities may namely depend on the tension of the host structure. Therefore, the amount of light reaching the light-sensitive system may be tuned by controlling the tension. Hence, this embodiment enables to optimize the signal as output by the light-sensitive system for further processing and thus allows fine control over the signal-to-noise ratio relative to the amount of disturbance of the host structure by the optically active entities. As a result, the spatial and temporal resolution may be tuned.

Furthermore, suppressing the motion of the host structure suppresses blurring of the image data due to this motion.

Furthermore, the force application system may be utilized to force the host structure into a known geometry. In an example, the force application system comprises two optical traps holding two respective beads between which a DNA molecule as host structure is connected. Then, the force application system may be controlled to position the beads such that the DNA molecule is known to be on a straight line between the beads. This advantageously allows for example efficiently scanning an excitation beam along this one dimensional straight line without the need to first image the host structure in two dimensions to find its orientation. Hence, undesired bleaching of the fluorophores may be prevented.

One aspect of this disclosure relates to an optical system for determining a presence of at least one guest structure, e.g. a protein or a complex of proteins, at a host structure, e.g. a DNA-molecule. The optical system comprises a light-sensitive system configured to receive light from the host structure hosting one or more optically active entities at at least one part of the host structure not hosting the at least one guest structure. The optically active entities cause light emission from said at least one part. The light-sensitive system is further configured to output a signal based on the received light. The optical system further comprises a data processing system configured to perform the step of determining a light value based on the output signal. The light value indicates an amount of light from the host structure being incident on the light-sensitive system. The data processing system is further configured to perform the step of determining on the basis of the light value at least one of a quantity and a position of the at least one guest structure at the host structure.

One aspect of this disclosure relates to a computer program comprising instructions which, when the program is executed by a computer, cause an optical system as described herein to execute one or more of the method steps as described herein.

One aspect of this disclosure relates to a computer-readable storage medium comprising instructions which, when executed by a computer, cause the computer to carry out one or more of the method steps as described herein.

One aspect of this disclosure relates to a method for enabling determination of at least one of a quantity and a position of at least one guest structure at a host structure. The method comprises combining the host structure hosting the at least one guest structure with a fluid and a plurality of optically active entities for causing the host structure to host one or more optically active entities at at least one part of the host structure not hosting the at least one guest structure, wherein the optically active entities cause light emission from said at least one part.

As will be appreciated by one skilled in the art, aspects of the present invention may be embodied as a system, a method or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a processor/microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present invention, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor and/or a central processing unit (CPU) and/or a graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

Moreover, a computer program for carrying out the methods described herein, as well as a non-transitory computer readable storage-medium storing the computer program are provided. A computer program may, for example, be downloaded (updated) to the existing data processing system or be stored upon manufacturing of these systems.

Elements and aspects discussed for or in relation with a particular embodiment may be suitably combined with elements and aspects of other embodiments, unless explicitly stated otherwise. Embodiments of the present invention will be further illustrated with reference to the attached drawings, which schematically will show embodiments according to the invention. It will be understood that the present invention is not in any way restricted to these specific embodiments.

BRIEF DESCRIPTION OF THE DRAWINGS

Aspects of the invention will be explained in greater detail by reference to exemplary embodiments shown in the drawings, in which:

FIG. 1A schematically shows an embodiment of an optical system according to one embodiment, FIG. 1B illustrates a method for according to an embodiment, FIG. 2 illustrates a host structure hosting a guest structure and an optically active entity according to an embodiment, FIG. 3 illustrates a method for determining the position of a guest structure according to an embodiment, FIG. 4A shows an actual image and image data obtained while performing a method according to an embodiment, FIG. 4B illustrates a manner for localizing a guest structure, FIG. 7 illustrates a number of applications for the method.

DETAILED DESCRIPTION OF THE DRAWINGS

Figures 5, 6:
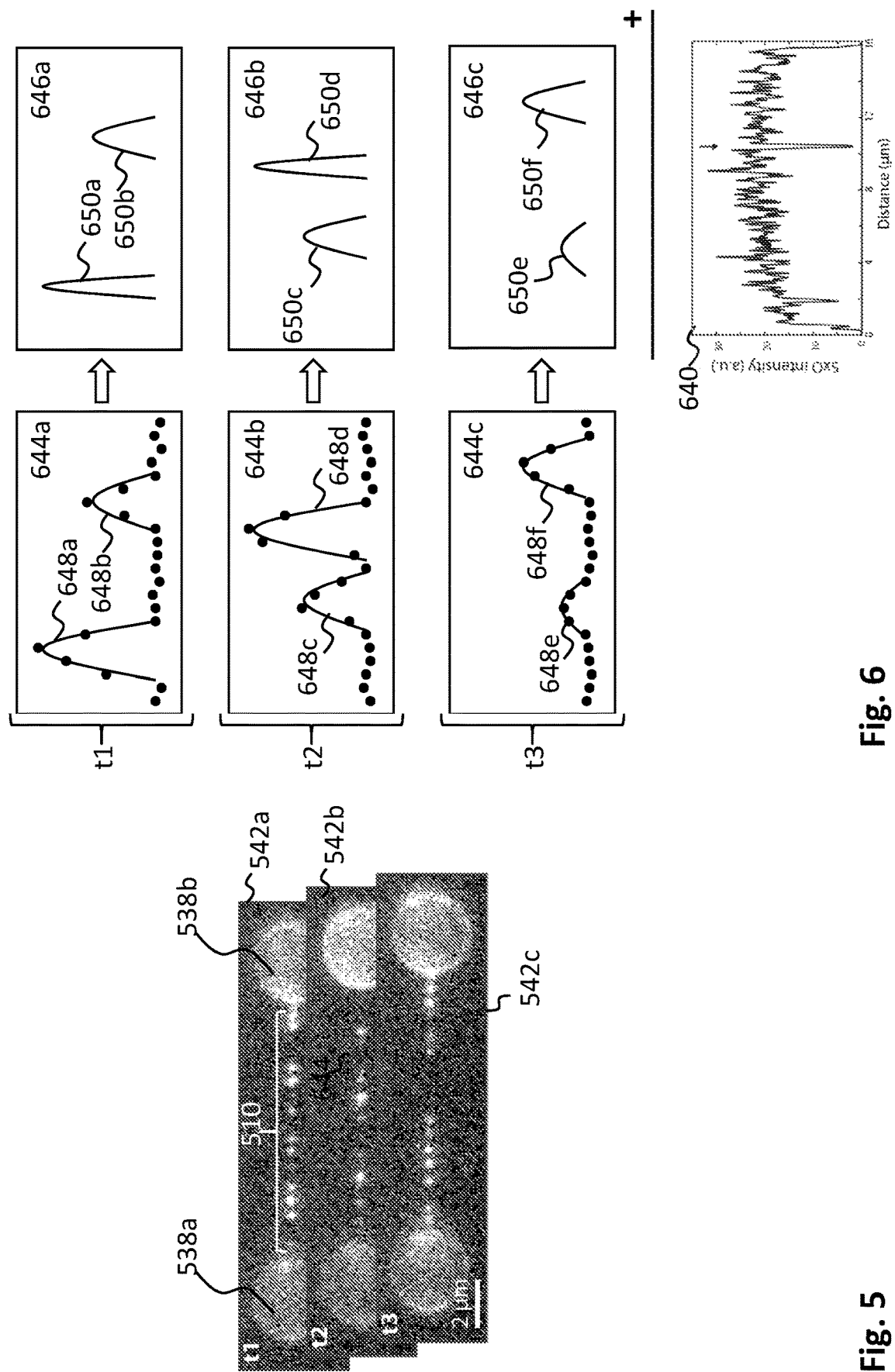
FIG. 5 shows actual images of a host structure obtained while performing a method according to an embodiment, FIG. 6 schematically shows determining image data based on event localization curves.

FIG. 1A schematically illustrates an optical system 100 according to one embodiment. The system 100 may be embodied as a microscope, for example at least one of a wide field microscope, a laser scanning microscope, a confocal microscope, a fluorescence microscope, a Stimulated Emission Depletion (STED) microscope and a Total Internal Reflection (TIRF) microscope. The optical system 100 comprises a light-sensitive system 102 and a data processing system 104. The light-sensitive system 102 may comprise a photo-detector and/or an imaging system, such as a camera, in particular a CCD camera such as an EMCCD camera and/or a position-dependent light sensor.

The optical system 100 may further comprise an excitation optical system comprising an excitation light source 101, such as an excitation laser, in particular a 491-nm laser, which excitation optical system is configured to direct excitation light 103 towards host structure 110 via dichroic mirrors DM1 and DM2. The excitation light 103 may excite the optically active entities that the host structure is hosting at parts not hosting the guest structure. These excited optically active entities may subsequently decay and emit a photon. Additionally or alternatively, the optically active entities may emit light as a result of electroluminescence and/or chemiluminescence. Additionally or alternatively, the optically active entities interact with the excitation light and thereby alter the properties and/or intensity of the transmitted and/or reflected light.

The light-sensitive system 102 is configured to receive light 106 from the host structure 110 via dichroic mirrors DM2 and DM1. To this end, the light-sensitive system 102 is for example positioned such that a light-sensitive part, such an imaging plane, is directed towards the host structure 110. The optical system 100 may comprise an objective lens 107 for focusing the excitation light 103 onto the host structure 110 and for collecting light 106 from the host structure 110.

The host structure 110 may be a DNA molecule and may be positioned in a sample holder 108. The optical system 100 may comprise such a sample holder in the form of a flow cell. The flow cell 108 may be a multichannel laminar flow cell that does not have a physical barrier between the channels enabling a fast buffer exchange between fluid flows respectively comprising beads, host structures, such as DNA, guest structures, such as proteins and/or protein complexes, and optically active entities, such as DNA intercalator molecules.

Host structure 110 may be a one-dimensional structure, such as DNA, single stranded DNA, RNA, a microtubule, actin, a carbon nanotube. The host structure 110 may also be a two-dimensional structure, such as a membrane, for example a cell membrane.

The host structure 110 is hosting one or more optically active entities (shown in FIG. 2), such as DNA intercalator molecules, at at least one part of the host structure not hosting a guest structure. The optically active entities cause light emission 106 from said at least one part. The light-sensitive system 102 is further configured to output a signal based on the received light 106. The optically active entities may be optically active in the sense that they are fluorescent and/or phosphorescent and/or luminescent and/or light absorbent, et cetera.

Preferably, the optical system 100 comprises a trap system 109 for establishing a trap, e.g. an optical, acoustical, magnetic trap or electrophoretic trap, that can hold a bead to which the host structure is connected. Optical traps are known in the prior art. An example of an optical trap is described in Ashkin A, Dziedzic J M, Bjorkholm J E, Chu S (1986) Observation of a single-beam gradient force optical trap for dielectric particles. Opt Lett 11:288. doi: 10.1364/OL.11.000288. An example of an acoustical trap is described in WO2014200341A1 with title "Molecular manipulation system and method", which is hereby incorporated by reference into this application.

In one embodiment, the trap system 109 comprises a trap light source 109a for generating trapping light. The trap light source 109a may be a 10 W 1064 nm CW fiber laser. Further, trap system 109 may comprise a module 109b for rotating the polarization of the trapping light and a polarizing beam splitter 109c for splitting the trapping light into two light beams, one for establishing a first trap and a second for establishing a second trap. The trap system 109 may comprise a module 109d for controlling the position of the first trap and a module 109e for controlling the position of the second trap. In particular, independent trap steering may be done via a coarse-positioning piezo stepper mirror and an accurate piezo mirror for the respective traps. A polarizing beam splitter 109f may be used to recombine the individually controlled trapping beams. If the trap system 109 is configured to establish two traps, advantageously the host structure 110 can be held fixed between two optically trapped beads.

Preferably, the optical system 100 comprises a force detection system 111, that is configured to detect a force exerted by at least one of the traps established by trap system 109 on a trapped entity. The system shown comprises a force detection module 111a for detecting a force exerted by the first trap and a force detection module 111b for detecting a force exerted by the second trap. As known in the art, these modules 111a and 111b may be position dependent sensors as the force can be determined based on a deflection of the trapping light and using back-focal plane interferometry.

The data processing system 104 is configured to perform a number of steps which will be explained with reference to FIG. 1B, which enable the optical system 100 to determine the presence of the at least one guest structure at the host structure 110. Furthermore, the data processing system 104 may be configured to control at least one of the light-sensitive system 102, the sample holder 108, the excitation optical system, in particular excitation light source 101, and the trap system 109, in particular at least one of the trap light source 109a, module 109b, 109c, 109d and 109e and a force detection system.

FIG. 1B illustrates a method according to one embodiment. The data processing system 104 is configured to perform at least steps 118 and 120. Furthermore, the data processing system 104 may be configured to control the light-sensitive system 102 to perform steps 114 and 116. To this end, the data processing system may transmit control signals to the light-sensitive system 102.

Step 112 depicts an optional step in an embodiment of the method comprising steps 114-120. However, in one distinct aspect, this disclosure relates to step 112, not necessarily in combination with any of the other steps 114-120.

Step 112 enables determination of at least one of a quantity and a position of the at least one guest structure at the host structure 110 and comprises combining the host structure 110 hosting the at least one guest structure with a fluid and a plurality of optically active entities for causing the host structure to host one or more optically active entities at at least one part of the host structure not hosting the at least one guest structure. As indicated above, the optically active entities cause light emission from said at least one part.

In a particular embodiment, the flow cell 108 comprises a plurality of laminar flows, a first flow comprising beads, a second flow comprising DNA molecules, a third flow comprising proteins or protein complexes, and a fourth flow comprising DNA intercalator molecules. In this embodiment, step 112 may comprise establishing two optical traps in order to capture two of the beads flowing in the first laminar flow. Then, the trapped beads may be moved to the second laminar flow, where one DNA molecule present in the second flow is tethered between the two beads. Then, the created dumbbell construct of the DNA molecule tethered between two optically trapped beads is moved into the third laminar flow, where one or more proteins as guest structures bind to the DNA molecule.

Finally, the assay is moved to the fourth laminar flow where the optically active entities in this flow transiently bind to parts of the DNA molecule that are not covered by the proteins or protein complexes. While the assay is in the fourth laminar flow, it may be imaged, for example by using widefield imaging and/or confocal scanning microscopy, wherein a confocal beam is used as excitation light to excite the optically active entities hosted by the host structure 110, which entities in response emit light towards the light-sensitive system 102.

Steps 114-120 schematically illustrate the method according to one embodiment. Step 114 comprises the light-sensitive system 102 receiving light 106 from the host structure 110 hosting one or more optically active entities at at least one part of the host structure not hosting the at least one guest structure. The optically active entities cause light emission 106 from said at least one part.

Step 116 comprises the light-sensitive system outputting a signal based on the received light. In an example, the light-sensitive system is an imaging system comprising a plurality of pixels, and in step 116 outputs, for each pixel, a signal that is indicative of an amount of light 106 that is incident on it. The light-sensitive system may output a voltage and/or current signal based on the received light. To this end, the light-sensitive system may comprise a photo-multiplier system for high accuracy. The light-sensitive system may alternatively or additionally comprise an avalanche photodiode and/or a camera, such as a CCD or CMOS camera.

Step 118, which may be performed by the data processing system 104, comprises determining a light value based on the output signal. The light value indicating an amount of light from the host structure being incident on the light-sensitive system. Determining a light value may comprise the steps of determining, based on a voltage output signal, a value and storing this value at a data storage of the data processing system.

Step 120, which may be performed by the data processing system 104 comprises determining on the basis of the light value at least one of a quantity and a position of the at least one guest structure at the host structure. Hence, with step 120 the presence of the at least one guest structure at the host structure is determined.

The method may be performed as a bulk measurement in the sense that the light value does not convey any spatial information. In an example, the light value indicates a total amount of light that is coming from the host structure 110 in its entirety. Then, based on this light value it can be determined how much guest structures are present at the host structure 110, for example in the sense that an average coverage of the host structure by the guest structure can be determined. After all, the more guest structures 122 are hosted by the host structure 110, the less parts on the host structure 110 are left from which light emission can occur. Determining a quantity of the guest structures at the host structure may thus be understood to relate to determining a fractional coverage of the host structure and does not necessarily involve determining the total number of guest structures that is hosted at the host structure. The above described bulk measurement may be implemented in a titration experiment for determining a binding affinity of the guest structure in respect of the host structure. Then, a fractional coverage of the host structure may be determined with varying solution conditions of the solution in which the assay is positioned.

The light value may be spatially resolved in the sense that it is associated with a specific part of the host structure. Typically a spatially resolved light value is part of image data comprising a plurality of spatially resolved light values, wherein the image data represent at least a part of the host structure 110.

In one embodiment, the method comprises determining a binding property of the at least one guest structure in respect of the host structure on the basis of the light value. Determining a binding property may require the quantity and/or the position of the at least one guest structure at the host structure.

The binding property may for example be determined by determining the rate at which the quantity of the at least one guest structure changes in time. In an embodiment, the host structure is moved from a first solution to a second solution. The first solution may comprise guest structures and the second solution may not comprise guest structure and may be a buffer solution. When, the host structure is positioned in the first solution, it may at some point host a first quantity of guest structures. The first quantity may be known and for example is a maximum quantity that the host structure can host. Then, when the host structure is positioned in the second solution, the guest structures that are present at the host structures and that have thus also been brought into the second solution, may subsequently recede from the host structure, for example because the guest structures unbind from the host structure. As a result, the host structure can host more optically active entities, which may be understood to be present in the first solution as well as in the second solution, and thus more light may be emitted by the host structure. In this method, the faster the guest structures recede from the host structure, the faster the amount of light emitted from the host structure will change upon moving the host structure from the first to the second solution. The rate at which guest structures recede from the host structures may correspond to an off-rate constant of the guest structures in respect of the host structure. In this embodiment, the quantity of the guest structures is determined in the sense that a change of the quantity is determined.

This embodiment further allows to determine a binding isotherm, which may be understood to be the quantity of guest structures hosted by the host structure as a function of a concentration of the guest structures in a fluid at a fixed temperature. Further, the dependence of the binding property of the guest structures in respect of the host structure on at least one of the following parameters may be studied: (i) the tension of the host structure, (ii) the salt concentration of a fluid wherein the host structure and guest structure(S) are positioned, (iii) a temperature, for example of a fluid wherein the host and guest structures are positioned.

FIG. 2 schematically illustrates a host structure 210 hosting at least one guest structure 222. In one example, the host structure 210 is a double stranded DNA molecule and the guest structure 222 is a protein bound to the DNA molecule. The host structure comprises at least one part 228 that does not host the guest structure and a part 230 hosting the guest structure.

The host structure 210 may host the guest structure 222 in the sense that the host structure 210 comprises binding sites, to which the guest structure can bind, and has bound at one or more of its binding sites at least one guest structure 222. Furthermore, the host structure 222 hosts an optically active entity 224, which may be a DNA intercalator molecule.

The host structure 210 may be at least partially positioned in a fluid comprising optically active entities 226 that are not bound to the host structure 210, but that can bind to the host structure, at least at parts at which no guest structure 222 is bound. The fluid for example is present in sample holder 108. In particular, the optically active entities 226 may be configured to transiently bind to the host structure 210. Furthermore, the optically active entities, which may thus be DNA intercalator molecules, may exhibit a significantly increased quantum yield when bound than when unbound thereby causing very limited amount of background fluorescence. In an example, the fluorescence of the optically active entities enhances with a factor ranging between 500-1000 when hosted by the host structure 210.

In one embodiment, the entities exhibit an off-rate with respect to the at least part of the host structure, which off-rate is equal to or larger than a rate at which events of a process under scrutiny occur. In an example, the process concerns the separation of two strands of a DNA molecule by a helicase repeatedly performing a step of separating at least one base pair at a time. Herein, the rate at which the event occurs may then relate to the number of times this separating step is performed per unit of time. The equilibrium binding constant may be defined as a ratio between an on-rate and the off-rate with respect to the at least part of the host structure. The off-rate may be tuned through the choice of ionic strength of the fluid comprising the host structure. This embodiment advantageously reduces perturbations of the structure and/or reduces perturbations of dynamic processes involving the structure, such as enzymes processing along DNA, because the entities only shortly bind to the at least part of the structure. The binding time may advantageously be (tuned to be) shorter than the characteristic time of the process under study in order to reduce perturbation of this process. The off-rate preferably is at least equal to, more preferably larger than, most preferably at least ten times larger than the rate at which the events of the process of interest occur. For example, if a polymerase steps at a rate of 100-1000 Hz, then it would be advantageous if the off-rate is larger than 1000 to 10000 Hz to leave each step relatively unperturbed. In another case, for example, where the average translocation rate of this polymerase would be of interest, then the average intercalator coverage is preferably considered to correct for the chance of encountering an intercalator. To illustrate, if a polymerase can on average travel ~10 bases before it encounters an intercalator, then the off-rate should be equal to or larger than the stepping rate of the polymerase for the impact of the intercalator on the rate to be less than −10%.

In one embodiment, the optically active entities are configured to bind to parts of the host structure 210 that are not covered by the one or more guest structures 222 and to, when bound to the host structure 210, emit light. Hence, the optically active entities bound to the host structure cause light emission from parts of the host structure that are not covered by the at least one guest structure.

In a particular embodiment, the optically active entities 224 are fluorescent dyes that bind to bare DNA, but not to protein-bound DNA regions. The optically active entities may be nucleic acid stains, in particular carbocyanine nucleic acid stains, and/or monomeric cyanine nucleic acid stains, such as YO-PRO1 and YO-PRO3 shown in FIG. 2, and/or SYTOX molecules, for example SYTOX™ Blue, SYTOX Green, SYTOX Orange, SYTOX AADvanced, SYTOX Red, as offered by the firm ThermoFisher. The optically active entities for example are YO-PRO (YO-PRO) mono-intercalators that have relatively high off-rates ($>>100$ $s^{-1}$, for example 1100 $s^{-1}$) and sufficient photo stability. Additionally or alternatively, the optically active entities are Sytox Orange (SxO) intercalators. SxO exhibits off-rates ($k_{off}$) in the 1 $s^{-1}$ range at 15 pN tension applied to the host structure, which provides sufficient time to acquire on average 100-600 photons from a single binding event in order to do localization microscopy. For optimization of the experimental parameters these kinetic binding rates can be tuned over up to 7 orders of magnitude depending on type of optically active entity, ionic strength of the fluid comprising the host structure, and the tension applied to the host structure. The optically active entities may also be fluorescently labeled transiently binding proteins and/or species that diffuse along the host structure, such as XLF. Transient interactions such as transient binding may, at least to a lesser extent, perturb the host structure 210.

In one embodiment (not shown), the host structure 210 comprises or is a membrane, such as a cell membrane. As known, a membrane may comprise a double layer of lipid molecules. In this embodiment, the membrane may be understood to host a guest structure, for example a protein or protein complex, by having the guest structure embedded in and/or bound to the membrane. The optically active entities 226 may be fluorescently labelled lipid molecules, which can be introduced in the membrane and which are, as is typical for lipid molecules in a membrane, able to diffuse rapidly through the membrane. However, such a rapidly diffusing, fluorescently labelled lipid molecule may not be able to move through parts of the membrane that are hosting a guest structure such as a protein or protein complex. If the fluorescently labelled lipid molecule is continuously excited and thus continually emits light, the labelled lipid molecule thus causes light emission only from parts of the membrane that are not hosting a guest structure.

In one embodiment, a fractional occupation, e.g. a fractional coverage, of the host structure 210 by the optically active entities 224 is below 20%, preferably below 15%, more preferably below 10%, most preferably below 5%.

An optically active entity 224, while being hosted by the host structure 210 may either possess an ON state, in which it causes light emission from the part at which it is hosted, or an OFF state, in which it does not cause light emission although being hosted by the host structure 210.

The fractional coverage may be defined as a ratio between an amount of optically active entities 224 being hosted by host structure 210 and an amount of optically active entities 224 that the host structure 210 can (approximately) maximally host. Herein, the amount of optically active entities 224 hosted may be understood to include both entities in the ON state and in the OFF state. In a particular example, the fractional coverage may be defined as a ratio between an amount of binding sites of the host structures having bound an optically active entity and a total amount binding sites at the host structure.

The fractional coverage may be controlled by controlling at least one of (i) a concentration of optically active entities in a fluid in which the host structure is positioned and (ii) a tension on the host structure and (iii) a salt concentration of the fluid in which the host structure is positioned. In case the optically active entities comprise intercalator molecules, it is noted in respect of controlling the tension that a higher tension corresponds to more intercalator binding and in respect of controlling the salt concentration that a higher salt concentration corresponds to less intercalator binding.

A baseline experiment may be performed in order to enable determination and control of the fractional coverage. This experiment may comprise saturating the host structure 210 with optically active entities, wherein the host structure 210 does not comprise any guest structure. Subsequently, a light value indicative of the amount of light from the saturated host structure may be determined. When determining the light value, a correction may be performed for background light, which correction may comprise subtracting a background intensity. Then, it may be assumed that the fractional coverage scales linearly with the measured amount of light, especially when there is no self-quenching. As a result, the concentration of the optically active entities and/or the tension of the host structure and/or the salt concentration may be varied while monitoring the fractional coverage (by monitoring the amount of light from the host structure). Hence, the influence of these parameters on the fractional coverage may be determined, which allows to control the fractional coverage during the methods disclosed herein for keeping it below a desired percentage and/or close to a desired percentage.

As indicated, the light-sensitive system may be part of a microscope, e.g. a fluorescence microscope. FIG. 3 illustrates the method according to one embodiment. Herein, steps 312, 314 and 316 are similar to respective steps 112, 114 and 116 described with reference to FIG. 2. Furthermore, steps 318 and 320 are specific embodiments of respective steps 218 and 220 described with reference to FIG. 2.

Step 318 comprises determining image data based on the output signal. The image data represent an image of at least part of the host structure and comprise a plurality of image pixel values associated with respective parts of the host structure. Each image pixel value indicates an amount of light from its associated part of the host structure incident on the light-sensitive system.

FIG. 4 shows an image 432 of a host structure 410, in particular a DNA molecule 410, that is held between two optically trapped microspheres 438a and 438b, e.g. polystyrene beads, herewith forming a dumbbell construct. Producing such a dumbbell construct may comprise producing a biotinylated DNA construct from bacteriophage 2 DNA and positioning it in a flow cell where spontaneous binding of biotinylated DNA to streptavidin-coated polystyrene microspheres (4.65 μm diameter) occurs.

The two optical traps holding the respective microspheres may be generated using a 10 W 1064 nm CW fiber laser. Trap separation and recombination may be achieved using two polarizing beam-splitter cubes. Independent trap steering may be done via a coarse-positioning piezo stepper mirror and an accurate piezo mirror. Two 300 mm lenses may be used to couple the laser beams into a water-immersion objective.

Graph 440 shows the determined image data and in particular on the vertical axis the light intensity in arbitrary units and on the horizontal axis the position in micrometers, wherein the position of zero micrometers corresponds to the point at which the host structure, the DNA molecule 410, connects to microsphere 438a.

Image 432 was captured using a 491-nm laser as excitation light source and intercalator molecules YO-PRO were used as optically active entities.

Step 320 comprises determining at least one region of interest (ROI) 430 comprising at least one image pixel value in the image on the basis of the image pixel values, wherein the at least one ROI 430 in the image indicates the position of the at least one guest structure at the host structure 410. As shown, the ROI appears as a relatively dark area in the image 432 along the DNA molecule 410.

This embodiment enables to determine binding and unbinding rates of individual molecules ($k_{on}/k_{off}$) based on distributions of the binding and unbinding times.

This embodiment also enables to identify whether a guest structure covers a host structure in a continuous or discontinuous manner.

Furthermore, this embodiment may comprise determining a binding property of the guest structure in respect of the host structure in the sense that this embodiment may comprise at least one of determining a mobility of the guest structure on the host structure, determining a processivity of the guest structure on the host structure, a speed of the guest structure moving in respect of the host structure, on/off binding rates of guest structures, a footprint of a single molecule on the host structure, filaments of guest structures, a degree of cooperativity between two guest structures in respect of the host structure.

In FIG. 4, the image comprises three regions of interest 430a, 430b, and 430c as indicated by the circular areas at positions of approximately 1 micrometer, 2 micrometer and 10.5 micrometer respectively. At these positions respective guest structures are thus present. Hence, step 320 may comprise determining a first (430a) and second (430b) ROI in the image on the basis of the image pixel values. The first and second ROI each comprise at least one image pixel value and the first ROI (430a) in the image indicates a position of a first guest structure at the host structure 410 and the second ROI (430b) in the image indicates a position of the second guest structure at the host structure 410.

Optionally, step 320 comprises determining that said at least one image pixel value of the ROI is indicative of an amount of light that is lower than a threshold amount of light. The regions of interest 430a, 430b and 430c for example appear in the image 432 as relatively dark spots, or shadows, on the host structure 410 and appear as negative peaks in graph 440. A fit, e.g. a Gaussian fit, of the negative peak associated with ROI 430c has a standard deviation of 114 nanometers.

The image 432 may be regarded as an inverse image of the positions at which the host structure 410 is hosting guest structures in the sense that these positions appear as dark spots as opposed to bright spots as may be the case when the guest structures would be labeled.

Optionally, step 320 comprises determining a threshold pixel value indicating the threshold amount of light on the basis of the image data. Herein, the step of determining that said at least one image pixel value is indicative of the amount of light lower than the threshold amount of light comprises comparing the at least one image pixel value with the threshold pixel value.

The threshold light value may be determined by determining an average and a variation of image pixel values that are associated with respective parts of the host structure not hosting a guest structure and then, based on the determined average and variation, determining the threshold pixel value. In an embodiment, the threshold pixel value may be calculated as:

$$Th = avg - N*stdev, \text{ wherein}$$

Th is the threshold pixel value, avg and stdev are indicative of the average and standard deviation respectively of the image pixel values associated with bare host structure (not hosting a guest structure) and N is a constant that may be selected, in an example N equals 3. In this embodiment, image pixel values that are lower than the threshold pixel value are identified as belonging to a Region of Interest. Choosing a high value for N advantageously reduces the number of false-positives, but increases the minimal size of the guest structure that can be detected. Herein a false-positive may be understood to be an identification of a region of interest that incorrectly indicates a part of the host structure hosting a guest structure.

Further, determining the average, avg, and variation, e.g. stdev, of image pixel values associated with parts of the host structure not hosting a guest structure may be performed in several manners. One manner comprises first determining a preliminary average, avg_prelim, and a preliminary variation, for example a preliminary standard deviation, stdev_prelim, of the obtained image pixel values and determining a preliminary threshold image pixel value, Th_prelim, based on these values, for example according to the formula:

$$Th\_prelim = avg\_prelim - N\_prelim*stdev\_prelim.$$

Then, based on this preliminary threshold image pixel value one or more image pixel values are discarded, for example the ones having lower values than the preliminary threshold image pixel value. Subsequently, by determining the average and variation of the remaining image pixel values, the average, avg, and variation, stdev, are determined based on which the threshold pixel, Th, value can be determined as per above.

Preferably, N is larger than N_prelim and/or the threshold Th is lower than the preliminary threshold Th_prelim, because, preferably, all image pixel values associated with parts hosting a guest structure are discarded. Discarding some image pixel values associated with parts not hosting a guest structure does not severely impact determination of the threshold pixel value Th. For determining the threshold pixel value, a larger N may be chosen in order to reduce the number of false positives, i.e. the number of times an ROI is falsely determined, which would be the case when an ROI would be determined without a guest structure being hosted at the position indicated by this ROI.

Another manner for determining the average and variation of image pixel values associated with parts of the host structure not hosting a guest structure comprises performing a baseline measurement which will be explained in more detail with reference to FIG. 8.

In one embodiment, the method comprises determining a mobility of the guest structure in respect of the host structure on the basis of a plurality of determined positions of a guest structure. Herein, the mobility may be a measure of the ability of the guest structure to move along, over and/or through the host structure. To this end, the method may comprise determining on the basis of a plurality of light values, each value being indicative of an amount of light from the host structure being incident on the light-sensitive system at a plurality of time instances, a moving position of at least one guest structure at the host structure and determining the mobility based on the moving position of the at least one guest structure. This embodiment optionally comprises associating a first determined position of a guest structure at a first time instance to a second determined position of the guest structure at a second time instance, for example in the sense of determining that both the first position and the second position relate to the same guest structure.

Furthermore, clustering of guest structures may be determined, for example, the method may comprise determining whether guest structures bind individually or form clusters and/or filaments.

In one embodiment, the method comprises determining the region of interest by identifying image pixel values in the image data that are below or above the determined threshold value. Then, for determining the location of the region of interest, and thus of the guest structure at the host structure, the image pixel values in the region of interest are fitted with a guest structure localization curve, which may be Gaussian curve.

FIG. 4B shows a selection of the image pixel values of image data 440 as dots. The figure in particular shows image pixel values 431*a* associated with region of interest 430*c* that are below a determined threshold value Th and image pixel values 431*b* also associated with region of interest 430*c*, but that are above the determined threshold pixel value. In this example, region of interest 430*c* has been determined by identifying that the image pixel values 431*a* are below the threshold image pixel values. Then, these image pixel values 431*a* as well as neighboring image pixel value 431*b* have been fitted to a guest structure localization curve 433, in this example a Gaussian curve. Then, the guest structure at the host structure may be determined to be positioned at the position of the tip of the guest structure localization curve 433. This allows to accurately determine the position of the guest structure. By executing this method a plurality of times, a movement of the guest structure on the host structure can be accurately determined.

In one embodiment, the method comprises controlling a force application system to apply a tension to the host structure 210 for controlling the signal that is output by the light-sensitive system. The effective resolution of the method can be enhanced by applying tension to the host structure to suppress e.g. its thermal fluctuations. In particular, to improve the effective resolution of images of the host structure to a value better than the diffraction-limit (e.g. by localization microscopy) the inventors find that a tensile force is preferred. It is noted that effective FWHM (=resolution) of the guest localization curves may decrease with applied tension, improving the accuracy of the method. The force application system may comprise a system for establishing a trap, such as an optical trap, such as a holographic optical trap, an acoustical trap and an electrical trap such as an Anti-Brownian Electrokinetic trap. It may also comprise an Acoustic Force Spectroscopy (AFS) system for creating acoustical standing waves in order to attract objects to the nodes of this standing wave and thereby apply forces on the objects. The host structure 410 may be connected to at least one bead 438*a*, 438*b* that sits in such trap established by the force application system. In an example, the structure 410 is connected to two trapped beads 438*a*, 438*b*. In these cases, controlling the force application system may comprise controlling the relative positions of the traps holding the beads. It should be understood that the force application system may be any kind of system that can cause a force or a change of force acting on the host structure 410. An example of a force application system would thus be a manipulation system for deforming the at least part of the structure. Additionally or alternatively, magnetic tweezers and/or flow stretching may be used for applying a force.

The host structure 410 may be at least partially positioned in a flow cell. The force application system may then comprise the flow cell (not shown). Furthermore, controlling the force application system may in such case comprise controlling at least one of a fluid flow and a solution of a fluid in the flow cell, for example to control a drag force acting on the host structure 410. The solution of the fluid may be controlled in the sense that the ionic strength of the solution is controlled.

In one embodiment, controlling the force application system comprises controlling the force application system to change a force acting on the structure 410. A change of the force may be achieved by a change of position of acoustical/optical/electrical traps relative to each other. A change of force may be achieved by varying the amplitude or wavelength of an acoustic standing wave. A change of the force may be achieved by changing at least one of a fluid flow and a solution of the fluid.

As discussed above, the binding kinetics of optically active entities such as intercalator molecules depend on tension on the host structure 410. When optically active entities bind very briefly to the host structure, a relatively high temporal resolution may be obtained in the sense that it may be easier to determine a movement of a guest structure. In an example a temporal resolution of 190 ms is obtained, which suffices for observing the 1D-sliding motion of protein complexes along a DNA molecule. However, longer binding times may cause a relatively high spatial resolution in the sense that more photons are emitted by the host structure per single optically active entity. Thus, the method may comprise controlling the force application system to apply a tension to the host structure 210 for controlling the signal in order to control the spatial and/or temporal resolution of the method. Further, applying a tension to the host structure may decrease the fluctuations of the host structure, and thus of the optically active entities present at the host structure, which may yield a higher spatial resolution.

Controlling the force application system may be performed based on a force measurement that indicate a current tension of force applied to the host structure. If the current tension is higher or lower than a desired tension, then the force application system may be controlled to decrease or increase the applied force respectively. The force measurement may be performed using back-focal-plane interferometry and may comprise collecting the light using a condenser lens and separating the two trapping paths with a polarizing beam-splitter cube and two position-sensitive detectors.

Further, salt concentration and type of optically active entity may be adapted to control the spatial and temporal resolution of the method, because these parameters also influence the binding kinetics as discussed.

These kinetic binding rates can be tuned over up to 7 orders of magnitude depending on type op optically active entity, ionic strength of the fluid comprising the host structure, and the tension applied to the host structure.

FIG. 5A shows three images 542a, 542b and 542c representing the host structure 510 during three time periods t1, t2 and t3. In this case, the host structure is a 15.8 micrometer DNA molecule captured between two beads. Single binding events of optically active entities (SYTOX Orange DNA intercalators) are visible as dots between the beads. A 532-nm excitation laser was used to excite the Sytox Orange molecules.

FIG. 6 schematically shows an embodiment for determining image data 640, depicted as image data 440 in FIG. 4. On the left-hand side are shown three subsets of image data 644a, 644b and 644c. The horizontal axis of these graphs indicates position and the vertical axis indicates light intensity.

These subsets of image data are determined based on the output signal for different time periods t1, t2 and t3. Each dot in the graph represents an image pixel value and indicates an amount of light from its associated part of the host structure in the sense that each dot indicates a number of photons incident on the light-sensitive system during the time period of the subset per position along the DNA molecule. The image data 640 may be determined based on these subsets of image data 644a, 644b and 644c as will be explained in more detail below.

Each subset 644a, 644b and 644c of image pixel values comprises a plurality of image pixel values associated with a light-emitting event during the time period. A light-emitting event may comprise the transient binding of an optically active entity and the repeated excitation of the entity followed by the emission of a photon. To illustrate, subset 644a comprises image pixel values associated with a light-emitting event 648a and image pixel values associated with light-emitting event 648b. Furthermore, subset 644b comprises image pixel values associated with light-emitting event 648c and image pixel values associated with light-emitting event 648d. Subset 644c comprises image pixel values associated with light-emitting event 648e and image pixel values associated with light-emitting event 648f.

Then, for each light-emitting event 648a-648f in the subsets of image data, a point spread function is fitted to the associated image pixel values. The fitting comprises selecting an amplitude of the point spread function. In FIG. 6, the image pixel values associated with light-emitting events 648a-648f are fitted with a particular point spread function.

Herein the width of this point spread function was not adapted for fitting, merely the amplitude of the point spread function. As shown, light-emitting event 648a is fitted with the point spread function having a far larger amplitude than the point spread function that fits light-emitting event 648e.

Then, as indicated by the arrows, for each light-emitting event in the subsets of image data, based on the selected amplitude for fitting the point-spread function and optionally based on a selected width for fitting the point-spread function, an event localization curve 650 is determined. The localization curve 650 indicates a position of the light-emitting event. The event localization curve may indicate the position of the light-emitting event in the sense that it indicates a mean position and an associated variance. In one embodiment, the event localization curves are normalized Gaussian profiles. The variance of the Gaussians may then be calculated using a formula for localization uncertainty as, for example, described in (Mortensen et al., *Nature Methods*, 2010, 7, 377-381)

$$\text{Var}(\mu_x) = \frac{\sigma_a^2}{N}\left(\frac{16}{9} + \frac{8\pi\sigma_a^2 b^2}{Na^2}\right).$$

Where $\sigma_a^2 = \sigma^2 + a^2/12$ with $\sigma$ given by the standard deviation of the point spread function and a the pixel size. N is the number of photons collected and b is the background noise. This formula stipulates that the more photons are detected for a light-emitting event, the smaller the variance is. This is reflected by the event localization curves 650 in FIG. 6. Note for example that the event localization curve 650a is narrower, i.e. has a smaller variance, than event localization curve 650e, which is in accordance with the amplitude of the fitted point spread function being larger for light-emitting event 648a than for light-emitting event 648e.

Then, as indicated by the plus-sign, the image data 640 is determined by summing the determined event localization curves. As the determined image data is based on (Gaussian) fits, in principle any resolution for the image pixel values (shown as dots in FIG. 4B) in the image data may be chosen.

Alternatively, determining the image data 640 comprises summing the image pixel values in the subsets of image data 644a, 644b and 644c. Then, no event localization curves need to be determined, which allows for faster processing. The accuracy may be sufficient for measuring kinetics of the guest structure with respect to the host structure.

The image data 640 may also be determined as follows (not shown). In a first step a pixel grid having pixels of a particular size is chosen that is smaller than the best expected localization accuracy. Then, based on the location determined by the event localization curve a pixel closest to that event is activated. Optionally, instead of activating a pixel, for each localization, one count may be added to the pixel closest to that location. Even further, for each localization a predetermined Gaussian curve, having a predetermined width, may be plotted onto the predetermined pixels of the image data.

For determining the image data 440 shown in FIG. 4, a=130 nm and b=5.2. The standard deviation of the point spread function can be calculated by $s = 0.25\lambda/NA$, where $\lambda$ is the light wavelength ($\lambda$=570 nm for SxO emission) and NA the numerical aperture of the objective (NA=1.2).

The image data 440 shown in FIG. 4 was acquired over a period of 1 hour and 40 minutes. In this particular experiment $5.0 \cdot 10^4$ light-emitting events were localized over a length of 15.8 micrometer DNA, corresponding to a localization density of 3 nm$^{-1}$. A light-emitting event may be understood to be a binding of an optically active entity to the host structure.

In order to improve the spatial resolution of the method, the coverage rate may be kept low. To illustrate, if two light-emitting events occur simultaneously and very close to each other, the point spread function fits of these two events would overlap. Simultaneously may be understood as during a single time period associated with one particular subset of image data. In such case, there may be an image pixel value in the particular subset of image data that is associated with both light-emitting events, which prevents an accurate point spread function fit to either of the light-emitting events. Therefore, the coverage rate may be kept sufficiently low so that it is unlikely that two light-emitting events occur simultaneously within a particular distance of each other. The particular distance may correspond to a width of the point spread function of the light-sensitive system, e.g. 300 nm, that ensures that two point spread function fits in one subset of image data do not overlap significantly. In case the host structure is a DNA molecule, choosing the particular distance to be 300 nm would mean that less than one binding event occurs per 1000 base pairs, which would correspond to a fractional coverage of less than 0.1%. Preferably, the fractional coverage is even lower because when the fractional coverage in this example would be 0.1%, the binding events must be evenly spatially distributed else point spread functions would still overlap.

FIG. 7 illustrates that the methods disclosed herein enable a range of other interesting applications. The narrow footprint of (mono)intercalators of about 2 base pairs permits detection of small gaps or discontinuities in protein-filaments (the guest structures) even on nearly saturated DNA (the host structure). Intercalator binding in between protein filaments can thus be used to estimate the average uninterrupted filament length. For FIG. 7A a DNA as host structure was nearly completely saturated with a RAD51 protein as guest structure. When the RAD51-saturated DNA was exposed to YO-PRO binding, a clear sparse binding pattern of the intercalator was observed as shown in FIG. 7A, which is consistent with the protein forming a discontinuous structure on the DNA. The peak-to-peak distance in the intensity profile provided an estimate for the maximum RAD51 filament length of 1 kbp, which is in good agreement with previous estimates from AFM data (Ristic et al. 2005). Imaging the proteins themselves would in this case not yield any information, since the fluctuations in the fluorescent signal would be too small to give estimates for the filament length. In this way, the method yields information about protein architecture that was inaccessible from imaging the proteins themselves.

Furthermore, the methods described herein may be employed to visualize protein dynamics on dsDNA. In particular, FIG. 7C is a kymograph showing dark patches caused by bleached XLF multimers that move along a DNA with a time resolution of 190 ms.

Figures 8, 9:
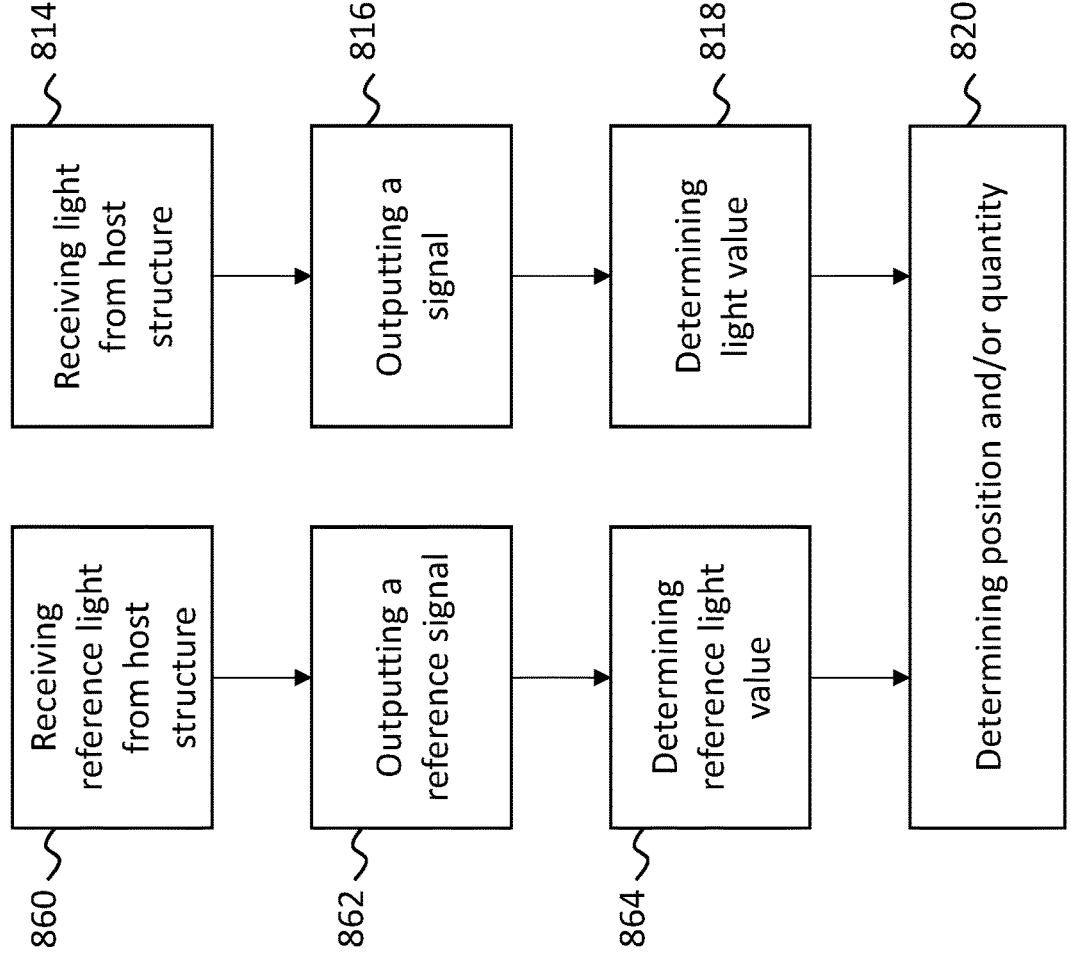
FIG. 8 illustrates a method involving a baseline experiment according to an embodiment.
FIG. 9 depicts a block diagram illustrating an exemplary data processing system according to an embodiment.

FIG. 8 illustrates a method according to one embodiment. Herein, steps 814, 816, 818 and 820 are similar to steps 114, 116, 118 and 120 as described above. Steps 860, 862 and 864 may be performed before or after steps 814, 816 and 818 are performed.

Step 860 comprises the light-sensitive system receiving reference light from the host structure hosting one or more optically active entities. The optically active entities cause light emission from the host structure and the host structure hosts a reference quantity of guest structures, e.g. does not host any guest structures.

Step 862 comprises the light-sensitive system outputting a reference signal based on the received reference light and step 864 comprises determining a reference light value based on the output signal. The reference light value indicates an amount of light from the host structure being incident on the light-sensitive system.

Of course, in case the light-sensitive system comprises an imaging system, step 864 may comprise determining reference image data based on the reference signal, wherein the reference image data represent an image of at least part of the host structure and comprising a plurality of reference image pixel values associated with respective parts of the host structure. Each reference image pixel value then indicates an amount of light from its associated part of the host structure incident on the light sensitive system. In such an embodiment, the above-described average and variation of image pixel values may be determined based on the these determined reference image pixel values. After all, these reference image pixel values are associated with parts of the host structure not hosting a guest structure.

In this embodiment, step 820 comprises determining on the basis of the light value and of the reference light value at least one of the quantity and the position of the at least one guest structure at the host structure.

It may be that a host structure itself, without hosting a guest structure, comprises parts that cannot host any optically active entities, irrespective of whether a guest structure is present at these parts or not. In an example, the host structure has a particular structure, which impedes guest structures to bind at certain parts. If not for such a baseline measurement, such parts may be falsely identified as hosting a guest structure, which would negatively impact the accuracy of determining the quantity and/or position of guest structures at the host structure.

FIG. 9 depicts a block diagram illustrating an exemplary data processing system which the optical system as described herein may comprise.

As shown in FIG. 9, the data processing system 970 may include at least one processor 972 coupled to memory elements 978 through a system bus 976. As such, the data processing system may store program code within memory elements 978. Further, the processor 972 may execute the program code accessed from the memory elements 978 via a system bus 976. In one aspect, the data processing system may be implemented as a computer that is suitable for storing and/or executing program code. It should be appreciated, however, that the data processing system 970 may be implemented in the form of any system including a processor and a memory that is capable of performing the functions described within this specification.

The memory elements 978 may include one or more physical memory devices such as, for example, local memory 980 and one or more bulk storage devices 982. The local memory may refer to random access memory or other non-persistent memory device(s) generally used during actual execution of the program code. A bulk storage device may be implemented as a hard drive or other persistent data storage device. The processing system 970 may also include one or more cache memories (not shown) that provide temporary storage of at least some program code in order to reduce the number of times program code must be retrieved from the bulk storage device 982 during execution.

Input/output (I/O) devices depicted as an input device 984 and an output device 986 optionally can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 9 with a dashed line surrounding the input device 984 and the output device 986). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 988 may also be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 970, and a data transmitter for transmitting data from the data processing system 970 to said systems, devices and/or networks. Modems, cable modems, and Ethernet cards are examples of different types of network adapter that may be used with the data processing system 970.

As pictured in FIG. 9, the memory elements 978 may store an application 990. In various embodiments, the application 990 may be stored in the local memory 980, the one or more bulk storage devices 982, or apart from the local memory and the bulk storage devices. It should be appreciated that the data processing system 970 may further execute an operating system (not shown in FIG. 9) that can facilitate execution of the application 990. The application 990, being implemented in the form of executable program code, can be executed by the data processing system 970, e.g., by the processor 972. Responsive to executing the application, the data processing system 970 may be configured to perform one or more operations or method steps described herein.

Various embodiments of the invention may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 972 described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention claimed is:

1. A method for determining a presence of at least one guest structure at a host structure, the method comprising steps of:
    receiving light from the host structure at a light sensitive system, wherein the host structure is hosting one or more optically active entities at at least one part of the host structure not hosting the at least one guest structure, wherein the optically active entities cause light emission from said at least one part of the host structure,
    outputting an output signal by said light sensitive system based on the received light,
    determining a light value based on the output signal, the light value indicating an amount of light from the host structure incident on the light-sensitive system, and
    determining on the basis of the light value, at least one of a quantity and a position of the at least one guest structure at the host structure.

2. The method according to claim 1, further comprising a step of:
    determining a binding property of the at least one guest structure in respect of the host structure on the basis of the light value.

3. The method according to claim 1, wherein the light-sensitive system is part of a microscope, the method comprising:
    determining image data based on the output signal, the image data representing an image of at least part of the host structure and comprising a plurality of image pixel values associated with respective parts of the host structure, wherein each image pixel value indicates an amount of light from its associated part of the host structure incident on the light-sensitive system; and
    determining at least one region of interest (ROI) comprising at least one image pixel value in the image on the basis of the image pixel values, wherein the at least one ROI in the image indicates the position of the at least one guest structure at the host structure.

4. The method according to claim 3, wherein determining the at least one ROI in the image comprises determining that said at least one image pixel value of the ROI is indicative of an amount of light that is lower than a threshold amount of light.

5. The method according to claim 4, further comprising a step of:
    determining a threshold pixel value indicating the threshold amount of light on the basis of the image data, and wherein the step of determining that said at least one image pixel value is indicative of the amount of light lower than the threshold amount of light comprises comparing the at least one image pixel value with the threshold pixel value, and wherein determining the threshold pixel value comprises
    determining an average and a variation of image pixel values that are associated with respective parts of the host structure not hosting a guest structure; and
    determining the threshold pixel value based on the determined average and variation.

6. The method according to claim 3, wherein determining the image data based on the output signal comprises
  determining for a plurality of time periods respective subsets of image data based on the output signal, wherein each subset of image data represents an image of at least part of the host structure during respective time periods, each subset of image data comprising a plurality of image pixel values associated with respective parts of the host structure, wherein each image pixel value in a subset of image data indicates an amount of light from its associated part of the host structure that is incident on the light-sensitive system during its associated time period, and
  determining the image data based on the subsets of image data.

7. The method according to the claim 6, wherein
  each subset of image pixel values comprises a plurality of image pixel values associated with a light-emitting event during the time period, and wherein
  determining the image data based on the subsets of image data further comprises:
  fitting a point spread function for each light-emitting event in the subsets of image data, to its plurality of image pixel values for determining a position of each light-emitting event;
  determining on the basis of the fitted point spread function for each light-emitting event in the subsets of image data, an event localization curve indicating a position of the light-emitting event, and
  determining the image data comprising summing the determined event localization curves.

8. The method according to claim 1, wherein a fractional occupation of the host structure by the optically active entities is below 20%.

9. The method according to claim 1, further comprising
  receiving reference light by the light-sensitive system from the host structure hosting one or more optically active entities, wherein the optically active entities cause light emission from the host structure and wherein the host structure hosts a reference quantity of guest structures,
  outputting, by the light-sensitive system, a reference signal based on the received reference light,
  determining a reference light value based on the output signal, the reference light value indicating an amount of light from the host structure incident on the light-sensitive system, and
  determining on the basis of the light value and of the reference light value at least one of the quantity and the position of the at least one guest structure at the host structure.

10. The method according to claim 1, wherein
  the host structure is at least partially positioned in a fluid comprising optically active entities, the optically active entities being configured to transiently bind to the host structure.

11. The method according to claim 1, further comprising applying a tension to the host structure by controlling a force application system, for at least one of
  controlling the signal that is output by the light-sensitive system, and
  suppressing a motion of the host structure.

12. The method according to claim 1, wherein
  the at least one guest structure comprises a protein and/or protein complex, and/or
  the host structure is a DNA molecule, and/or
  the optically active entities are DNA intercalator molecules, and/or
  the light sensitive-system comprises an imaging system.

13. An optical system for determining a presence of at least one guest structure at a host structure, the optical system comprising:
  a light-sensitive system configured to receive light from the host structure hosting one or more optically active entities at at least one part of the host structure not hosting the at least one guest structure, wherein the optically active entities cause light emission from said at least one part, and to output a signal based on the received light, and
  the optical system further comprising a data processing system configured to perform the steps of:
  determining a light value based on the output signal, the light value indicating an amount of light from the host structure incident on the light-sensitive system, and
  determining on the basis of the light value at least one of a quantity and a position of the at least one guest structure at the host structure.

14. The optical system according to claim 13, further comprising at least one of
  an excitation light source for generating excitation light for exciting the one or more optically active entities hosted by the host structure,
  a sample holder for holding the host structure,
  a sample holder comprising a flow cell,
  a first optical system for directing the excitation light towards the host structure,
  a first optical system comprising a condenser lens for focusing the excitation light on the host structure,
  a second optical system for directing light from said at least one part of the host structure to the light-sensitive system,
  a second optical system comprising an objective lens,
  a trap system for trapping at least one body in a trap attached to the host structure and
  a force detection system for determining a force exerted by the trap on the trapped body.

15. A method for enabling determination of at least one of a quantity and a position of at least one guest structure at a host structure, the method comprising
  combining the host structure hosting the at least one guest structure with a fluid and a plurality of optically active entities for causing the host structure to host one or more optically active entities at at least one part of the host structure not hosting the at least one guest structure, wherein the optically active entities cause light emission from said at least one part.

16. The method according to claim 1, wherein the guest structure is a protein and/or protein complex and the host structure is a DNA-molecule.

17. The optical system according to claim 13, wherein the guest structure is a protein and/or protein complex and the host structure is a DNA-molecule.

18. The method according to claim 7, wherein the point spread function is a point spread function associated with the light-sensitive system, and wherein the fitting comprises selecting an amplitude and/or width of the point spread function.

19. The method according to claim 12, wherein the DNA intercalator molecules are selected from the group consisting of YO-PRO molecules, SYTOX molecules and combinations thereof, and
  the light sensitive-system comprises an imaging system selected from a CCD camera and a CMOS camera.

20. The method of claim 14, wherein the trap is an optical and/or acoustic trap, and the trap system comprises means for positioning the trap.

\* \* \* \* \*